United States Patent [19]
Brugnara et al.

[11] Patent Number: 5,273,992
[45] Date of Patent: Dec. 28, 1993

[54] METHOD FOR REDUCING SICKLE ERYTHROCYTE DEHYDRATION AND DELAYING THE OCCURRENCE OF ERYTHROCYTE SICKLING IN-SITU

[75] Inventors: Carlo Brugnara, Newton Highlands; Seth L. Alper, Boston, both of Mass.

[73] Assignee: Beth Israel Hospital Assoc. Inc., Boston, Mass.

[21] Appl. No.: 970,929

[22] Filed: Nov. 2, 1992

[51] Int. Cl.$^5$ .............................................. A61K 31/415
[52] U.S. Cl. ..................................... 514/398; 514/396; 514/399; 514/815
[58] Field of Search ................ 514/396, 398, 399, 815

[56] References Cited

U.S. PATENT DOCUMENTS 4,343,808  8/1982  Broersma, Jr. et al. ............. 514/815
4,696,937  9/1987  Sebille et al. ........................ 514/398

OTHER PUBLICATIONS

Swamy et al., Chem. Abstracts CA85(9):56689d, 1976.
Chang et al., Medline 83244512(NLM), May 1983.

*Primary Examiner*—S. J. Friedman
*Assistant Examiner*—William Jarvis
*Attorney, Agent, or Firm*—David Prashker

[57] ABSTRACT

The present invention provides a chemical class of active compounds to be used as efficacious drugs in the treatment of sickle cell disease. The active compounds include imidazole derivatives, nitroimidazole derivatives, and triazole derivatives. These compounds are to be administered by any preferred route of administration including oral, intramuscular, intravenous, and any other parenteral route. If desired, these drugs may also be administered transmucosally, or subcutaneously, or using a dermal patch on the skin. In addition, the methodology is effective for both long term and short term therapy; may be employed prophylactically and/or therapeutically; and may be used in emergency, acute crisis clinical situations.

8 Claims, 4 Drawing Sheets

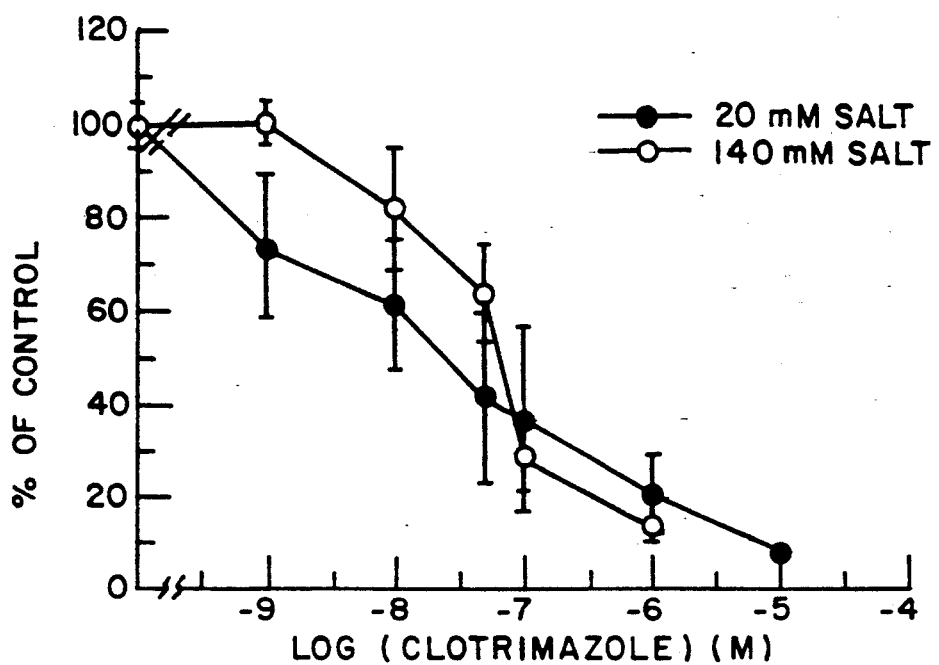
FIG. 1
FIG. 2
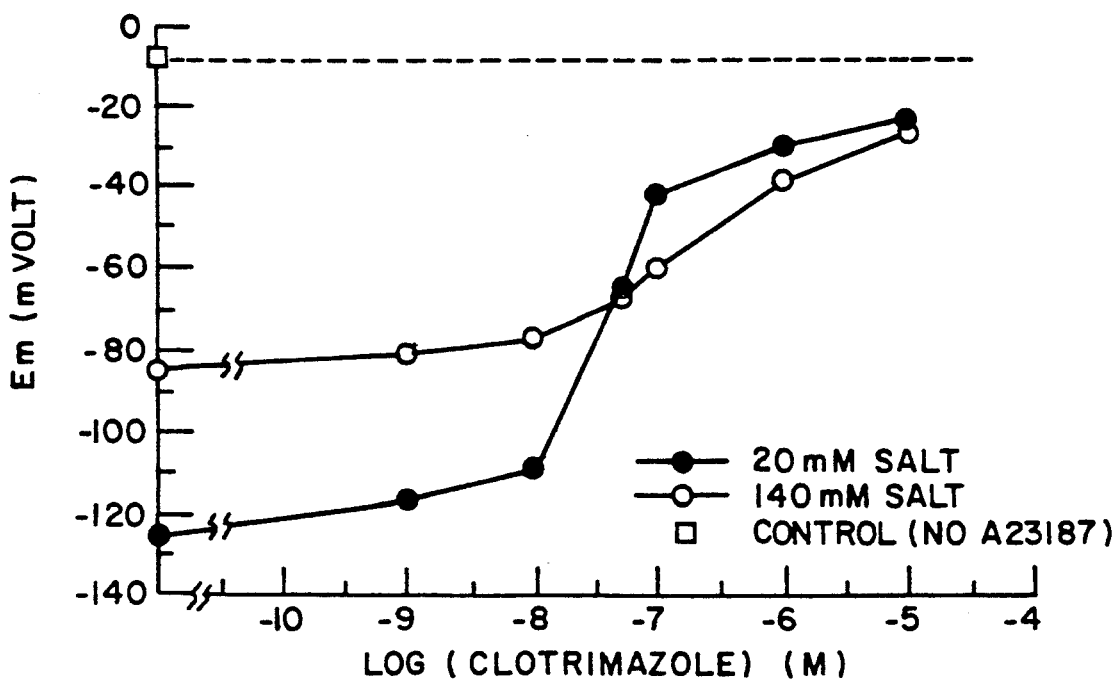

MEAN 113.1 33.7
28.4 5.3

MEAN 104.5 38.2
26.0 5.1

METHOD FOR REDUCING SICKLE ERYTHROCYTE DEHYDRATION AND DELAYING THE OCCURRENCE OF ERYTHROCYTE SICKLING IN-SITU

RESEARCH SUPPORT

The research investigations for the present invention were supported by Grant Number 2-P60-HL15157 from the National Institutes of Health.

FIELD OF THE INVENTION

The present invention is concerned with effective treatments of sickle cell diseases and the clinical pathologies and manifestations resulting thereby; and is particularly concerned with effective treatments for reducing sickle erythrocyte dehydration and delaying the occurrence of erythrocyte sickling in the microcirculation of the afflicted human.

BACKGROUND OF THE INVENTION

Although sickle cell disease and its clinical manifestations has been recognized within West Africa for several centuries, the first report of sickle cell anemia appearing in the medical literature occurred only in 1910 when James B. Herrick documented the presence of anemia in a 20-year-old black male using photomicrographs illustrating the presence of "thin sickle-shaped and crescent-shaped" red cells [Arch. Intern. Med. 6:517 (1910)]. Other cases of sickle cell disease were then continually recognized and reported over the next forty years until when in 1949 it was unequivocally confirmed that patients with sickle cell anemia had an electrophoretically abnormal hemoglobin, whereas those with the "sickle trait" had equal amounts of the normal and abnormal hemoglobin components. [Pauling, et al., *Science* 110:543-548 (1949)]. The inheritance pattern of other hemoglobin variants was subsequently clarified and provided convincing evidence that hemoglobin (Hb) S and hemoglobin (Hb) C are allelic variants of normal hemoglobin.

Sickle cell anemia and the existence of sickle hemoglobin (Hb S) was the first genetic disease to be understood at the molecular level; and is recognized today as the morphological and clinical result of the glycine to valine substitution at the No. 6 position of the beta globin chain [Ingram, V. M., *Nature* 178:792-794 (1956)]. The origin of the amino acid change and of the disease state is the consequence of a single nucleotide substitution [Marotta et al., *J. Biol. Chem.* 252:5040-5053 (1977)].

As sickle cell disease became better known and more easily identified, a remarkable degree of clinical heterogeneity in the physical manifestations and symptoms of sickle cell disease has become recognized. The anemia typically is of moderate severity and is usually well compensated by the dynamic steady state systems. The major source of mobidity and mortality is vaso-occlusion—which causes repeated episodes of pain in both acute and chronic form and also causes ongoing organ damage with the passage of time. Vascular occlusion often results in infarction of bone and/or bone marrow. Pulmonary and renal damage are frequently lethal in young adults; and cerebral infarction is often debilitating or fatal in children. Typically, patients afflicted with sickle cell disease are also very susceptible to bacterial infections and splenic dysfunction. Publications which describe the clinical and pathological manifestations in detail and review sickle cell disease are represented by the following: Clinton H. Joiner, *Cation Transport And Volume Regulation In Sickle Red Blood Cells*, American Journal of Physiology, 1992; Bunn, H. F. and B. G. FoRget, *Hemoglobin: Molecular, Genetic and Clinical Aspects*, U. B. Saunders Co., Philadelphia, 1986, Chapters 11 and 12, pages 453-564; Eaton, W. A. and J. Hofrichter, *Blood* 70:1245-1266 (1987); and Hebbel, R. P., *Blood* 77:214-237 (1991); and the reference cited within each of these publications.

It has long been recognized and accepted that the deformation and distortion of sickle cell erythrocytes upon complete deoxygenation is caused by polymerization and gelation of hemoglobin S. The phenomenon is well reviewed and discussed by Eaton and Hofrichter, *Blood* 70:1245 (1987). To gain some perspective on the problem and consequences of Hb S polymerization and intracellular gelation, it is useful to consider the events believed to occur as a red cell travels through the circulation of a patient afflicted with sickle cell disease. Erythrocytes containing no polymerized hemoglobin S in the arterial circulation may pass through the microcirculation and return to the lungs without sickling; or they may sickle in the veins; or they may sickle in the capillaries. For purposes of description, sickling is equivalent with intracellular gelation. The probability for each of these possible events for the sickle red cell will be determined by the delay time for intracellular gelation relative to the appropriate capillary transit time [Eaton et al., *Blood* 47:621 (1976)]. Thus, if it is thermodynamically impossible for intracellular gelation to take place, or if the delay time at venous oxygen pressures is longer than about 15 seconds, then cell sickling will not occur. Alternatively, if the delay time is between about 1 and 15 seconds, then the red cell will likely sickle in the veins. However, if the delay time is less than about 1 second, the red cell will sickle within the capillaries.

Note that for red cells that sickle within the capillaries, a number of possibilities exist as the consequent events—ranging from no effect on its transit time, to transient occlusion of the capillary, or to a more permanent blockage that may ultimately result in ischemia, or the infarction of the surrounding cells, and in destruction of the red cell. Which of these various possibilities and differing events will actually occur will depend on a number of factors: the total intracellular hemoglobin concentration; the composition of the intracellular hemoglobin; the rate and extent of deoxygenation; and the various transit times involved for the cells.

In addition, for unsickled red cells entering the microcirculation, a long capillary transit time will increase the probability of the potentially damaging vaso-occlusive events in two different ways. First, it will permit increased oxygen extraction which, in turn, will shorten the delay time. Second, it will increase the probability that a red cell with a given delay time will sickle within the capillary. Thus, for cells that either enter the microcirculation already sickled or become sickled within the microcirculation, there is a clear probability for occlusion of the small vessels; and the duration of an occlusion may be sufficiently long to compromise the oxygen supply to the surrounding tissues and hence alter the sickling and consequent vaso-occlusion in nearby microvessels. It is therefore critically important to recognize that vaso-occlusion is a dynamic process in which the fraction of capillaries that are occluded depends upon both rates of occlusion and the rate of capillary reopening. The factors that influence the transit times and the duration of occlusions thus play a critical role in the pathology in the sickle cell disease state.

It will also be noted and appreciated that the physical manifestations of sickle cell disease are paralleled by a cellular pathophysiology which is markedly diverse and varied. Certainly, much of the physiological dysfunction in sickle erythrocytes arises from the tendency of deoxy hemoglobin S to form an intracellular polymer—which results in a marked increase in cellular viscosity and impairment of rheological function. Sickle cells exhibit oxidative damage; abnormal adherence to endothelial cells, monocytes and other red cells; increased membrane rigidity; abnormal cytoskeleton function; deranged lipid structure; cation depletion and cellular dehydration; and abnormal carrier-mediated and passive permeability to cations.

Knowledge of the pathophysiology of sickle cells is merely one aspect of the continuing research interest in the physiology of erythrocyte generally. Considerable investigative efforts have focused upon the mechanisms of action and the various systems responsible for cation transport and volume regulation in normal red blood cells. In particular, the potassium transport pathways and the consequences of erythrocyte dehydration have been of major interest. A current summary of the various potassium transport pathways present in normal human erythrocytes is given by Table A below.

[Stuart, J. and J. C. Ellory, Brit. J. Haematol. 69:1-4 (1988)].

Thus, the potassium transport pathways and the consequences of erythrocyte dehydration affect a number of different cell attributes: the ageing of normal erythrocytes [Brugnara, C. and D. C. Tosteson, Am. J. Physiol. 252:C269-C276 (1987)]; the quality of erythrocytes while stored in anticoagulant preservative solutions in the Blood Bank [Wallas, C. H., Transfusion 19:210-215 (1979)]; dehydration of both normal and abnormal red cells [Clark et al., Blood 51:1169-1178 (1978); Bookchin et al., J. Clin. Invest., 87:113-124 (1991): and Lew et al., J. Clin. Invest., 87:100-112 (1991)]. Not surprisingly, as the different cationic transport mechanisms and pathways in human erythrocytes became known and better understood in detail, a variety of attempts were made to alter or influence the transport pathways. Merely representative of the reported attempts and to use various inhibitors to modify and alter the potassium transport pathways in human erythrocytes are those publications referenced and those inhibitors identified within Table A above. Clearly, different kinds and chemical classes of inhibitors have been experimentally investigated; and a range of different potencies for the various inhibitors were revealed. In addition, different modes of inhibition for the potassium transport pathways using a variety of different chemical agents have been reported in the literature. Merely representative of the current research

TABLE A

Potassium Transport Pathways in Human Erythrocytes*

| System | Mode | Maximal Capacity as K+ transporter (mmol/l.cells/h) | Inhibitor | Comments | Reference |
|---|---|---|---|---|---|
| NA+/K+ pump | Normally 3NA + 2K+ but partial fluxes occur | 1-3 | Cardiac glycosides (ouabain) | ATP-driven: operates at approx. 50% $V_{max}$ at normal cell [Na+] | Glynn, L. M., The Enzymes of Biological Membranes, 1985. |
| NaKCl contransport | 1Na+:1K+:2Cl— complex partial and exchange fluxes | 0.1-1.5 | Loop diuretics (bumetanide, furosemide) | Poised at close to equilibrium (i.e., zero net fluxes under physiological conditions) | Chipperfield, A. R., Clin. Sci. 71:465 (1986). |
| KCl cotransport | 1K+:1Cl— | >10 | Inernal divalent cations; loop diuretics at high concentrations | Highest in young cells; activated by NEM, pressure, cell swelling, acid pH. | Ellory, et al., Biomed. Biochem. Acta 46:531 (1987). |
| $Ca^{2+}$-activated K+ channel (Gardos channel) | Uncoupled K+ | >10 | Quinine | Activated by raised cell $[Ca^{2+}]$ | Lew & Ferreira Cur. Top. Memb. Transp. 10:217 (1978). |

*Source: Stuart, J. and J. C. Ellory, Brit. J. Hematol. 69:1-4 (1988).

It has long been recognized that the cytoplasm of the normal erythrocyte comprises approximately 70% water. Water crosses a normal erythrocyte membrane in milliseconds; however, the loss of cell water causes an exponential increase in cytoplasmic viscosity as the mean cell hemoglobin concentration (MCHC) rises above about 32 g/dl. Since cytoplasmic viscosity is a major determinate of erythrocyte deformability, the dehydration of the erythrocyte has substantial rheological consequences. Thus, the physiological mechanisms that maintain the water content of a normal erythrocytes, and the pathological conditions that cause loss of water from erythrocytes in the blood circulation, are critically important. Moreover, since cell water will follow osmotically any change in the intracellular concentration of ions, the maintenance of the red cell's potassium concentration is of particular importance investigations and publications in this field are the following: Turner et al. Vox Sanguinis 52:182-185 (1987); Alvarez et al., J. Biol. Chem. 267:11789-11793 (1992)]; Wolff et al., J. Membr. Biol. 106:243-252 (1988); Brugnara et al., J. Gen. Physiol. 100:47a (1992); Ellory et al., FEBS 296:219-221 (1992).

As regards sickle cell disease, the various attempts and approaches to therapeutically treating dehydrated sickle cells (and thus decreasing polymerization of hemoglobin S by lowering the osmolality of plasma) deserves special mention. The reported attemps have included the following approaches: intravenous infusion of distilled water [Knochel, J. T., Arch. Int. Med. 123:160-165 (1969)]; intravenous infusion of hypotonic saline [Gye et al., Am. J. Med. Sci. 266:267-277 (1973)]; administration of the antidiuretic hormone vasopressin together with a high fluid intake and salt restriction [Rosa et al., M. Eng. J. Med. 303:1138-1143 (1980);

Charache, S. and W. G. Walker, *Blood* 58:892–896 (1981)]; the use of monensin to increase the cation content of the sickle cell [Clark et al., *J. Clin. Invest.* 70:1074–1080 (1982); Fahim, M. and B. C. Pressman, *Life Sciences* 29:1959–1966 (1981)]; intravenous administration of cetiedil citrate [Benjamin et al., *Blood* 67:1442–1447 (1986); Berkowitz, L. R. and E. P. Orringer, *Am. J. Hematol.* 17:217–223 (1984); Stuart et al., *J. Clin. Pathol.* 40:1182–1186 (1987)]; and the use of oxpentifylline [Stuart et al., *J. Clin. Pathol.* 40:1182–1186 (1987)].

Despite these many reports and research investigations, all of them are fairly said to be complete failures in being proved to be highly toxic, impractical as either prophylactic or therapeutic treatment regimens, and/or producing side-effects which outweighed the benefits and value of using them. There remains, therefore, a longstanding and well recognized need for an effective method of treating sickle erythrocytes and sickle cell disease utilizing substances which are not cytotoxic in use concentrations, are effective, and avoid major side-effects and complications. The development of such a treatment methodology would be recognized by clinicians and research investigators alike as a major breakthrough and achievement in this technical field.

SUMMARY OF THE INVENTION

The present invention provides a method for reducing sickle erythrocyte dehydration and delaying the occurrence of erythrocyte sickling, said method comprising the step of administering an effective amount of at least one compound selected from the class consisting of imidazole, nitroimidazole, and triazole derivatives to sickle erythrocytes in-situ.

The method desirably employs imidiazole derivatives selected from the group consisting of clotrimazole, miconazole, ketoconazole, econazole, butoconazole, oxiconazole, sulconazole, and tioconazole; nitroimidazole derivatives selected from the group consisting of metronidazole, tinidazole, nimorazole, ornidazole, and benznidazole; and triazole derivatives selected from the group consisting of terconazole and itraconazole. Among these, clotrimazole, metronidazole, and econazole are the pharmacologically active compounds of choice.

BRIEF DESCRIPTION OF THE FIGURES

The present invention may be more easily and completely understood when taken in conjunction with the accompanying drawing, in which:

FIG. 1 is a graph illustrating the effect of clotrimazole on $Ca^{2+}$-activated $^{86}Rb$ influx in sickle erythrocytes;

FIG. 2 is a graph illustrating the effect of clotrimazole on the membrane potential ($E_m$) of sickle erythrocytes suspended either in low ionic strength or in normal saline in the presence of A23187 and 50 $\mu M$ $CaCl_2$;

DETAILED DESCRIPTION OF THE PRESENT INVENTION

Figure 3:
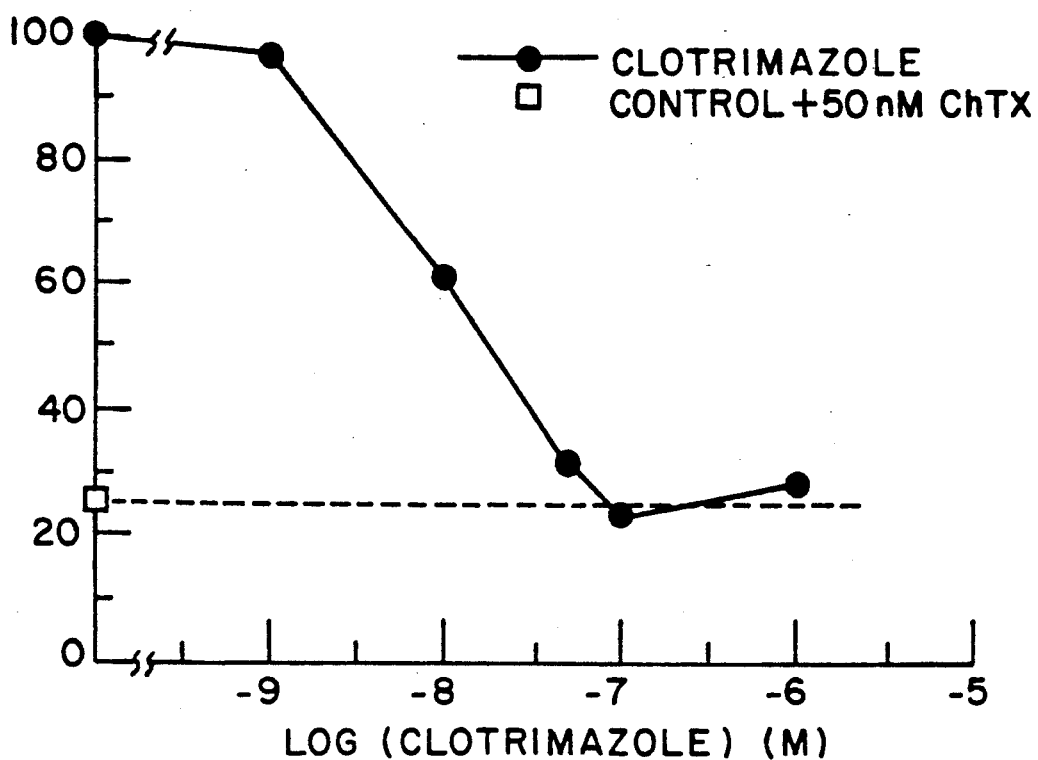
FIG. 3 is a graph illustrating the displacement of $^{125}I$-ChTx by clotrimazole in sickle erythrocytes.
Figure 4A:
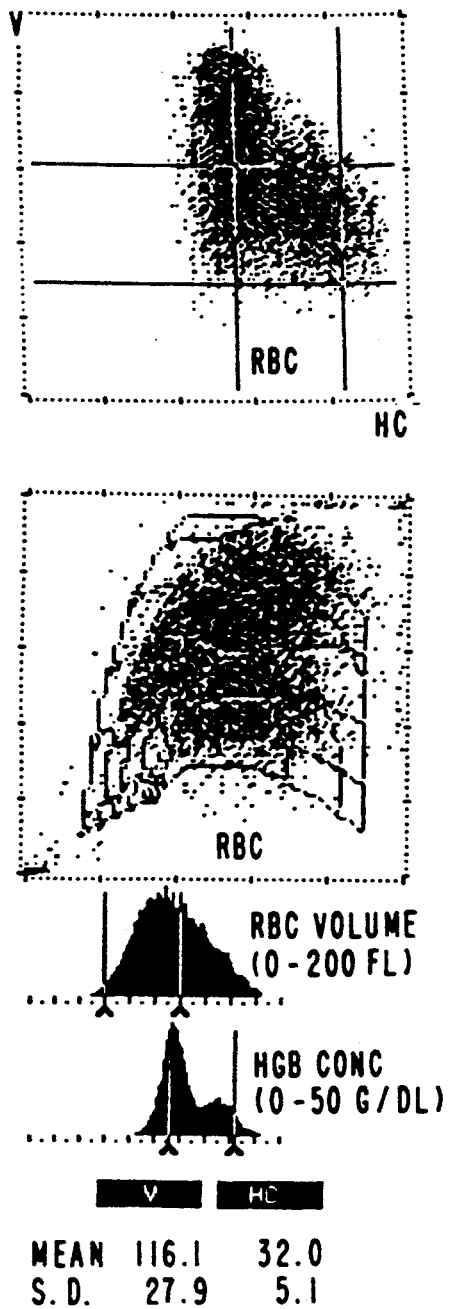
FIGS. 4A–4D are plots of the red blood cell volume and hemoglobin concentration measured with the H2-Technicon Blood Analyzer showing the effects of 10 $\mu M$ clotrimazole and of 50 nM ChTx on the dehydration of sickle cells incubated in the presence of 60 umol A23187/L cells and 100 $\mu M$ $CaCl_2$.
Figure 4B:
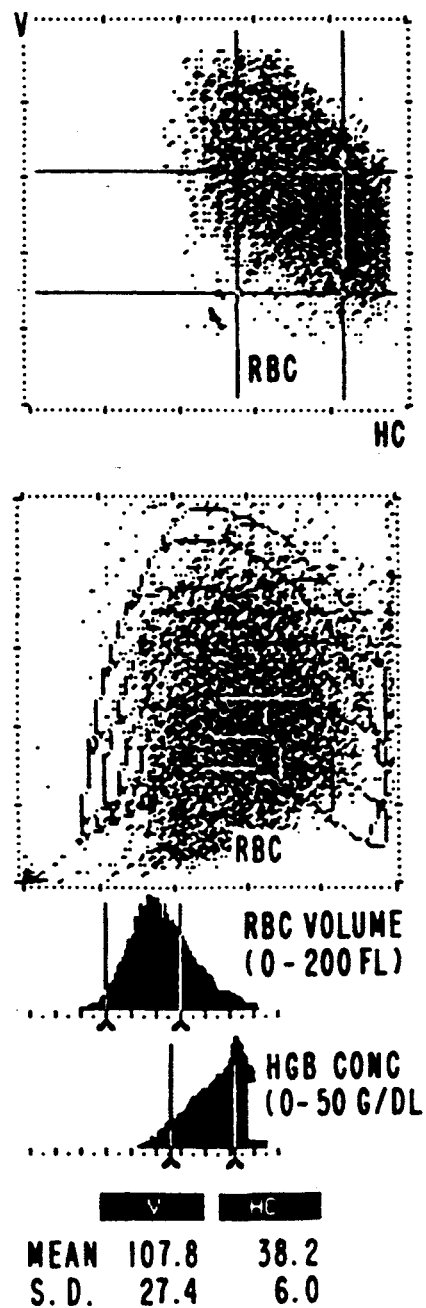
Figure 4C:
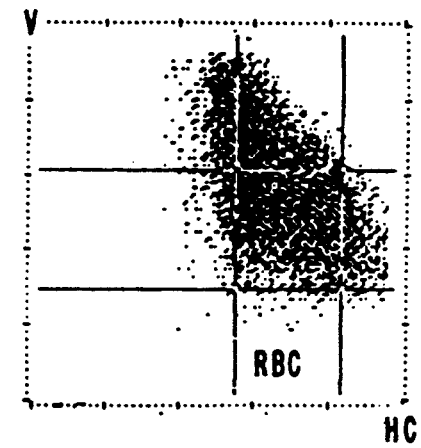
Figure 4C:
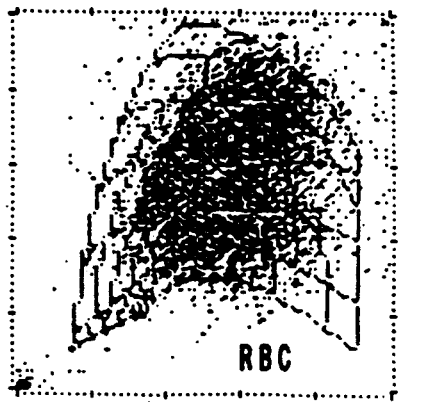
Figure 4C:
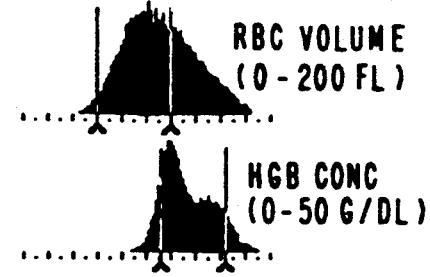
Figure 4D:
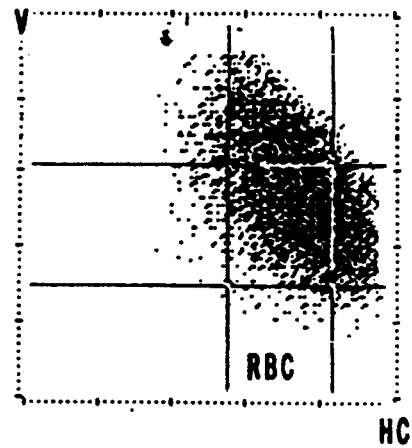
Figure 4D:
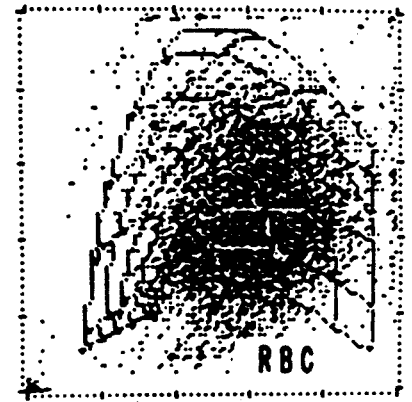
Figure 4D:
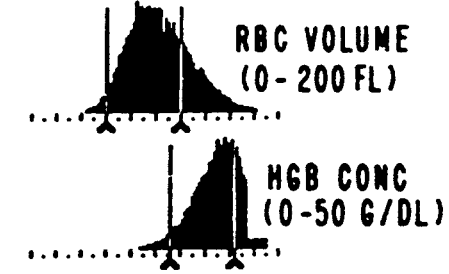

The present invention is a marked improvement and effective method for reducing sickle erythrocyte dehydration and delaying the occurrence of sickle erythrocyte distortion in-situ, and desirably in the microcirculation of human afflicted with sickle cell disease. By definition, the word "in-situ" encompasses and includes the terms "in-vivo", "ex-vivo", and "in-vitro" as these are commonly recognized and understood by persons ordinarily skilled in this field. Moreover, the term "in-situ" is employed herein in its broadest connotative and denotative contexts to identify an entity, cell, or tissue as found or in place—without regard to its source or origin, its condition or status, or its duration or longevity at that location or position. With this understanding and definition in mind, the various uses and multiple applications intended for the present invention may be properly recognized and appreciated.

In its broadest definition, the methodology comprises only a single step: the administration of an effective amount of at least one pharmacologically active compound to the sickle cells in-situ, this compound being selected from the class consisting of imidazole derivatives, nitroimidazole derivatives and triazole derivates. The administration of the active compounds in appropriate amounts will be able to induce nearly complete inhibition of the Ca-activated potassium (K) channel of sickle cells. The methodology thus offers major benefits and unique advantages to the clinician. These benefits and advantages include the following:

1. The active compounds to be administered to sicke erythrocytes in-situ and to humans afflicted with sickle cell disease are chosen from among imidazole, nitroimidazole and triazole derivatives. All of these chemical compositions are well recognized, pharmacologically characterized, and licensed for use by the FDA today as either antimycotic agents or antiprotozoal agents. As such, established and empirically documented parameters regarding their limited toxicity and their useful dosages as antimycotic and antiprotozoal agents are well described in the scientific and medical literature. In addition, there are few side-effects for any and no debilitating contraindications known for some of these chemical compounds. Accordingly, the chosen active compound may be administered immediately to effectively reduce the clinical manifestations and symptoms of sickle cell disease.

2. A variety of different modes of administration are intended to be used by the practitioner in the treatment of sickle cell disease when practicing the method of the present invention. While oral administration is the most preferred mode, parenteral administration by intravenous injection or infusion is available; as is subcutaneous injection, transmucosal, or transdermal administration using conventionally known articles and procedures. Unless the blood vessels and capillaries are very superficial and close to the skin, it is expected that topical administration, although available, will be the least effective mode of administration.

3. The method of the present invention may be used to treat sickle cell disease prophylactically to decrease hemoglobin S concentration and polymerization intracellularly; and thus diminish the time and duration of red cell sickling and vaso-occlusion in the blood circulation. In addition, the methodology may be used therapeutically in patients with acute sickle cell crisis via intramuscular or intravenous administrations. Finally, the method may be efficaously employed for treatment of chronic sickle cell episodes to control both the frequency and the duration of the crises.

4. The present invention also envisions and expects the user to choose dosages and routes of administration for a specific active compound in relationship to the degree of efficacy necessary for that specific clinical condition. Accordingly, if acute sickle cell crises are the dominant clinical manifestation, the most potent compound, clotrimazole, will be administered in relatively high concentration at multiple times during each day. Alternatively, if the patient exhibits only periodic sickle cell crises on an infrequent or irregular basis, it is more desireable to utilize a potent compound such as clotrimazole at minimal effective dose concentrations and using a less frequent regimen of administrations; or a less potent compound such as econazole or metronidaze. This will provide a therapeutic regimen commensurate with the severity of the sickle disease state. By choosing among the various active compounds and weighing the factors of potency, side-effects, and preferred administration mode, an effective prophylactic or therapeutic regimen can be planned which does not cause toxicity and yet is entirely effective to treat the clinical symptoms demonstrated by that particular patient.

In order to provide a complete understanding of the present methodology, and to present an orderly and comprehensive description of the subject matter as a whole which is the present invention, the detailed disclosure will be presented in successive sections as follows: a listing and description of the active compounds to be administered when practicing the present methodology; a disclosure of the pharmaceutical formulations, doses, and modes of administration intended to be used; and a presentation of experiments and empirical data demonstrating the efficacy and utility of the present invention.

I. THE ACTIVE COMPOUNDS TO BE ADMINISTERED

The present method requires the administration of at least one active compound selected from the class consisting of imidazole derivatives, nitroimidazole derivatives, and triazole derivatives to the sickle cells in-situ. Collectively, these compounds form a single chemical class of analogous structural formulations. Within the class as a whole, however, each derivative grouping has its own particular membership which share common structures and exhibit common properties. The chemical class as a whole, each group within the class, and the membership of each grouping is given by Table 1 below. In addition, preferred imidazole derivatives, nitroimidazole derivatives and triazole derivatives are described by structural formula and by specific published references indicating their conventionally known methods of synthesis and uses by Table 2 below.

TABLE 1

Groups and Examples of Pharmacologically Active Compounds

1. IMIDAZOLE COMPOUNDS
   Clotrimazole
   Miconazole
   Ketoconazole
   Econazole
   Butoconazole
   Oxiconazole
   Sulconazole
   Tioconazole
2. TRIAZOLE COMPOUNDS
   Fluconazole
   Terconazole
   Itraconazole
3. NITROIMIDAZOLE COMPOUNDS
   Metronidazole
   Tinidazole
   Nimorazole
   Ornidazole
   Benznidazole

TABLE 2

Preferred Examples of Pharmacologically Active Compounds

| NAME | STRUCTURAL FORMULA | REFERENCES |
|---|---|---|
| Clotrimazole; "Lotrimin"; "Mycelex" 1-[(2-chlorophenyl)diphenylmethyl]-1H-imidazole | | South African Patent No. 68/05,392 and 68/00,039; Plenipel et al., Antimicrob. Ag. Chemother. 271 (1969); Andytical Profiles of Drug Substances, Vol. 11, Academic Press, New York, 1982 pp. 225-255. Sawyer, et al., Drugs 9: 424-447 (1975) |
| Miconazole; "MONISTAT"; 1-[2-(2,4-dichlorophenyl)-2-[(2,4-dichlorophenyl) methoxyl]-1H-imidazole. | | Godefroi et al., J. Med. Chem 12: 784 (1969); U.S. Pat. No. 3,717,655; Brugsman et al, Arch. Dermatol. 102: 428 (170); Godts et al., Arzeimittel-Forsch 21: 256 (1961); Heel et al., Drugs 19: 7-30 (1980); |
| Ketoconazole; "NIZORAL"; 1-Acetyl-4[4-[[2-(2,4-dichlorophenyl)-2-(1H-imidazol-1-ylmethyl)-1,3-dioxolan-4-yl] methoxy]phenyl] pipeazine | | U.S. Pat. No. 4,144,346; U.S. Pat. No. 4,223,036; Levine, H. B. and J. M. Cobb, Am. Rev. Respir. Dis. 118: 715 (1978); and Rev. Infect Dis. 2: 519-692 (1980); Petersen et al, Ann. Intern. Med. 93: 791 (1980); Daneschmend, T. K. and D. W. Waknock, Clin. Pharm. 14: 13-34 (1988); |

TABLE 2-continued
Preferred Examples of Pharmacologically Active Compounds

| NAME | STRUCTURAL FORMULA | REFERENCES |
|---|---|---|
| Econazole; 1-[2-[(4-chlorophenyl) methoxyl]-2-(2,14-dichlorophenyl) ethyl]-1H-imidazole. | | Godefroi et al. J. Med. Chem 12: 784 (1969); U.S. Pat. No. 3,717,655; Thienpoint et al Arzneimittel-Forsch 25: 224 (1975); Heel et al Drugs 16: 177 (1978). |
| Tioconazole; 1-[2-[(2-chloro-3-thienyl)methoxy]-2-(2,4-dichlorophenyl)ethyl]-1H-imidazole. | | U.S. Pat. No. 4,062,966; Jevons, S. Antimicrob. Ag. Chemother. 15: 597 (1979); Odds, F.C., J. Antimicrob. Chemother. 6: 749 (1980); Kuokkanen, K., Mykosen 25: 274 (1982). |
| Butoconazole; "FEMSTAT"; | | Hajman, (1988); |
| Metronidazole; 2-methyl-5-nitroimidazole-1-ethanol | | U.S. Pat. No. 2,944,061; Cossar et al., Arzneimittel-Forsch 16: 23 9166); Bock, Arzneimittel-Forsch 11: 587 (1961); Ings et al. Biochem. Pharmacol. 15: 515 (1966); Brodgen et al., Drugs 16: 387 (1978). |

TABLE 2-continued

Preferred Examples of Pharmacologically Active Compounds

| NAME | STRUCTURAL FORMULA | REFERENCES |
|---|---|---|
| Terconazole; "TERAZOL" | | Kjaeldgaard, (1986); Hajman, (1988). |
| Itraconazole | | Dupont, B. and E. Drouchet, Rev. Inf. Dis. 9: 571-576 (1987); Van Cauteren et al., Rev. Inf. Dis. 9: 543-546 (1987); |

In addition, the user is directed to the published scientific papers, authoritative textbooks, and similar conventional medical references regarding the active compounds forming the chemical class as a whole. Merely representative of the range and variety of these publications are the following, the individual texts of which are expressly incorporated by reference herein: Goodman and Gilman, *The Pharmacological Basis Of Therapeutics*, eighth edition, MacMillan Publishing Company, 1990; Sawyer et al., *Drugs* 9:424–447 (1975); Seo et al., *Curr. Med. Res. Opin.* 5:169 (1977); Tettenborn, v. D., *Arzneim.—Forsch* 22:1272 (1972); Yap et al., *Arch. Intern. Ned.* 139:656–657 (1979); Tucker et al., *Antimicrov. Ag. Chem.* 32:369–373 (1988); Van Cauteren et al., *Rev. Infect. Dis.* 9:S43–S46 (1987); Daneshmend, T. K. and D. W. WarNock, *Clin. Pharmacok.* 14:13–34 (1988); and Heel et al, *Drugs* 19:7–30 (1980).

II. PHARMACEUTICAL FORMULATIONS, DOSES, AND MODES OF ADMINISTRATION

Compounds embodying the class of imidazole, nitroimidazole, and triazole derivatives can be administered for in-vitro treatment in any appropriate carrier for oral, intravenous, intramuscular, subcutaneous or parenteral administration. They can be introduced by any means that effects sickle erythrocytes in the blood of living humans. The in-vivo dosages administered will vary and be dependent upon the age, general health, and weight of the recipient; the kind of concurrent treatment, if any; the frequency of treatment; and the degree of the therapeutic effect desired. Generally, daily oral dosage of active compounds will be from about 0.01 milligram/Kg to 100.0 miligrams/Kg. Normally, from 50–500 milligrams per day, in one or more oral administration per day, is expected to be effective and should yield the desired results.

As compositions to be given intravenously, subcutaneously or parenterally, the chosen imidazole or triazole derivative compound will be prepared in sterile form; in multiple or single dose formats; and dispersed in a fluid carrier such as sterile physiological saline or 5% dextrose solutions commonly used with injectables. In addition, other methods of administration, such as transdermal applications, can be advantageously employed well.

Preferred Routes of Administration

The preferred route of administration will be oral. This will be the most convenient for patients. However, if some of the active drugs can be administered rectally or with a dermal patch, these alternative routes could be employed. Other routes available are transmucosal or subcutaneous, including depot and time release administrations. However, IV and IM routes should not be used for long term therapy and prophylaxis of sickling. They could be used in emergency situations.

Dosages and Frequency, Broad Dosage Ranges

Dosages are determined based on the measured inhibition of the Ca-activated K channel of red cells. Target plasma levels will be those capable to induce more than 75% inhibition. The percentage inhibition of the Ca-activated K channel of human red cells will be measured to assess appropriateness of achieved drug plasma levels. Dosage will be adjusted upward or downward to achieve the desired percentage inhibition. For clotrimazole, the dosages would be 1 gram per oral or more per day; conversely for ketoconazole, dosages could be between 100 and 400 mg taken once daily orally for adults.

| Major Side Effects: | |
|---|---|
| Clotrimazole: | Gastrointestinal (nausea, vomiting, diarrhea). Neurologic (due to Lysis of fungi and release of endotoxins in patients with fungal infections, and therefore maybe not applicable to sickle cell disease.) |
| Econazole: | Available only in topical formulation. |
| Metronidazole: | Headache, nausea, dry mouth and metallic taste. Occasional diarrhea, vomiting, and abdominal distress, some neurotoxic effect have been reported. Disulfiram-like effect based on experience with alcoholics. |
| Miconazole: | Has been shown to marrow hyoplasia in 40% of the use cases. This represents a strong argument against using this compound, which is the second most potent inhibitor in the imidazole class, in SS patients. Due to the already extremely high activity of the bone marrow to compensate for the anemia, a reduction in marrow's proliferative activity could lead to worsening anemia and increased need for blood transfusion. |

III. EXPERIMENTS AND EMPIRICAL DATA

To demonstrate the range and diversity of the active compounds employed using the present methodology, some illustrative examples are provided and experimentally evaluated below. These experiments and empirical data serve merely to demonstrate the range of the membership comprising the active compounds to be used with the present methodology. While the experimental design and described results are somewhat limited, it will be expressly understood that these empirical details do not either restrict or limit the class in any meaningful way. To the contrary, the empirical results and experiments are merely representative of the variety and diversity for the methodology which can be advantageously used in the treatment of sickle disease states.

A. Materials and Methods

Abbreviations: AA, normal subjects or red cells containing HbA; CCCP, carbonyl cyanide m-chlorophenyl hydrazone; ChTX, Charybdotoxin; CLT, clotrimazole; DIDS, di-isothiocyanodisulfonyl stilbene; EGTA, ethylene glycol tetra-acetic acid; HC, hemoglobin concentration; MCHC, mean corpuscular hemoglobin concentration; MCV, mean corpuscular volume; MOPS, 3-[N-morpholino]propanesulfonic acid; SS, subjects with sickle cell anemia, or red cells containing homozygous hbS.

Patient Selection

Patients homozygous for Hb S disease were selected. Blood was collected after obtaining informed consent from patients followed in the Hematology Division Clinic at Brigham and Women's Hospital and in the Boston Comprehensive Sickle Cell Center at Boston City Hospital. None of the patients had been transfused in the preceding 120 days.

Drugs and Chemicals

Synthetic charybdotoxin (ChTX) was purchased from Peptides International (Louisville, Ky). $^{125}$I-ChTX was purchased from New England Nuclear (Boston, Mass.). All preparations of $^{125}$I-ChTX were used within two months after radioiodination. A23187 was purchased from Calbiochem-Behring (La Jolla, Calif.). Sucrose was purchased from Serva Biochemicals, Paramus, N.J. Bovine Serum Albumin Fraction V was purchased from Boehringer Mannheim Biochemicals (Indianapolis, Ind.). Bumetanide was a gift from Leo Pharmaceutical Products (Ballerup, Denmark). Methazolamide (Neptazane ®) was a gift from Lederle Laboratories, Pearl River, N.Y. Fluconazole was provided by Pfizer Inc., Groton, Conn. Carbonyl cynide m-chlorophenyl hydrazone (CCCP), di-isothiocyanodisulfonic acid (MOPS), clotrimazole (CLT), miconazole, econazole, metronidazole, and all other drugs and chemicals were purchased from Sigma Chemical Co. (St. Louis, Mo.) and Fisher Scientific Co. (Fair Lawn, N.J).

Measurement of $^{86}$RB Influx in Human Red Cells

All red cells were incubated at room temperature in a medium containing 18 mM NaCl, 2 mM KCl, and 10 mM tris-HCl, pH 8.0, at a concentration of $1 \times 10^7$ cells/mL, in the presence of 100 mM ouabain, 10 mM bumetanide, and the desired amount of ChTx toxin. These experimental conditions maximize the binding of ChTX to human red cells. Other experiments were carried out in normal saline (140 mM NaCl, 2 mM KCl, 10 mM tris-HCl, pH 8.0). At the end of the incubation, triplicate samples of each cell suspension were spun at 3,000 g for 10 min. The supernatant was then removed and a smaller volume of medium containing A23187 (60 µM $CaCl_2$, and $^{86}$Rb was added to achieve a final Hct of 4-5%. Aliquots of cell suspension were taken at specified times (1, 3, and 5 min) and spun through 0.8 ml of medium with 5 mM EGTA and a 0.4 ml cushion of butyl-phthalate. The resultant supernatant and the upper layer of oil were carefully removed, the tube contents frozen at $-80°$ C. and the tube tip containing the cell pellet cut off and counted.

Measurement of $^{125}$I-ChTX binding to red cells

White cells were removed by passing 0.8 mL of packed red cells through a 5 ml syringe containing a mixture of equal parts of alfa-cellulose and microcrystalline cellulose as originally described by Beutler and West [*J. Lab. Clin. Med.* 88:328-333 (1976)]. Red cells were washed 3 times in binding medium containing 18 mM NaCl, 2 mM KCl, 10 mM tris-Cl, pH 8.0, 230 mM sucrose and 0.25% bovine serum albumin. A suspension was then made in the same medium at 15% Hct. Cells were added to 3.5 ml of binding medium containing $^{125}$I-ChTX to a final concentration of $1 \times 10^7$ cells/ml, in the absence or presence of the specified drugs. Tubes containing cell suspension were gently rotated for 90 min at room temperature. At the end of the incubation, aliquots of 1 ml were pelleted by microfuge and washed 3 times at 4° C. with a solution containing 200 mM NaCl, 10 mM tris-Cl, pH 8.0. The washed red cell pellet was then lysed in 1 ml of 0.01% Acationox ®, and counted in a gamma counter. Aliquots of binding medium were counted prior to addition of cells and at the end of the binding assay.

Measurement of membrane potential in red cells

Measurements of the proton distribution ratio in unbuffered media in the presence of the proton ionophore CCCP allow estimation of the red cell membrane potential ($E_m$). Erythrocytes were washed twice at room temperature with unbuffered medium of the desired composition and added with stirring to 5 ml of the same medium to a final Hct of 5%. All media contained 100 µM ouabain, 10 µM bumetanide, 10 µM DIDS, 10 µM methazolamide and 50 µM CCCP (50 mM stock solution in DMSO. The medium was maintained at 37° C., and pH was recorded for one min prior and 10 min following addition of the red cells. Inhibitors were added to the specified final concentration by appropriate dilution from 10 mM stocks. For internal pH measurements, 20 µl of 10% (v/v) Triton X-100 were added to the cell suspension in unbuffered medium under stirring, and the pH of the resultant lysate measured and assumed to equal $pH_i$. Em was calculated from the equation $$E_m = 2.3 \frac{Rt}{F}$$

[$pH_i-pH_o$], as detailed in Halpern et al, *Am. J. Physiol.* 257:c986-c996 (1989).

Measurement of $Ca^{2+}$-Dependent Erythrocyte Dehydration

Cells were incubated for 60 min at 37° C. in a medium containing 140 mM NaCl, 4 mM KCl, 100 µM $CaCl_2$, 1 mM K-phosphate buffer, pH 7.40, 10 mM tris-MOPS, pH 7.40, at 1-2% Hct. A23187 was subsequently added to a final concentration of 60 µmol/l cells under stirring. At the specified time intervals, the cell suspension was diluted with an equal amount of medium containing 5 MM EGTA and 0.1% BSA. The red cells were then washed four times with the same medium at 37° C. This procedure allowed for chelation of extracellular $Ca^{2+}$ and removal of A23187. An aliquot of cells washed in this medium was used to measure the distributions of cell volume and hemoglobin concentration with the H2-Technicon blood analyzer, while the remaining cells were washed four times with choline washing solution (144 mM Choline Cl, 1 mM $MgCl_2$, 10 mM tris-MOPS, pH 7.40 at 4° C.) for measurements of internal Na and K contents.

Measurements of $^{35}SO_4$ Influx Into AA Erythrocytes

The protocol used by Schofield et al. [*Nature* 355:836-838 (1992)] was used to measure $^{35}SO_2$- uptake in AA erythrocytes.

B. Results:

1. Inhibition of $Ca^{2+}$-activated $^{86}$Rb Influx BY Imidazole Antimycotics in SS Erythrocytes The inhibitory effect of clotrimazole (CLT) on the $Ca^{2+}$-activated $^{86}$Rb influx of SS cells was assessed in low ionic strength media (18 mM NaCl, 2 mM KCl, 230 mM sucrose) and in normal saline (140 mM NaCl, 2 mM KCl) in the presence of 60 µmol A 23187/L cell and 100 µM $CaCl_2$. As shown in FIG. 1, CLT markedly inhibited the $Ca^{2+}$-activated $^{86}$Rb influx. For red cells from each patient, the inhibition was greater in low ionic strength condition. Mean values of $ID_{50}$ (calculated with Dixon plot analysis) were 81.6±70 nM (n=3) for low ionic strength and of 143±60 (n=3) for normal saline.

Other antimycotics were tested for their inhibition of the $Ca^{2+}$-activated $^{86}$Rb influx in sickle erythrocytes. As shown in Table E1 below, the order of inhibitory potency was clotrimazole ($Ic_{50}$=86 nM) is equal to miconazole ($IC_{50}$=110 nM); and both of these were more potent than econazole ($IC_{50}$=270 nM). However, there was no inhibition by fluconazole. Note that the maximal inhibition of flux was significantly greater with clotimazole (87%) than with miconazole (63%). In addition, $^{86}$Rb influx was partially inhibited by metronidazole (IC$_{50}$=440 nM), a member of the nitroimidazole group; and only marginally by 10 μM ornidazole and tinidazole, 2 related compounds.

imidazole antimycotics which inhibit Ca$^{2+}$activated $^{86}$Rb influx are also capable of displacing $^{125}$I-ChTX from sickle erythrocytes--as shown by Table E1. There is reasonably good agreement between the IC$_{50}$ values of flux inhibition and $^{125}$I-ChTX displacement for the active inhibitors tested.

TABLE E1*

Inhibition of Ca$^{2+}$-Activated $^{86}$Rb Influx and Displacement of $^{125}$I-ChTX Binding in Sickle Erythrocytes

| Medium: | Inhibition of $^{86}$Rb influx 20 mM salt | | 140 mM Salt | | $^{125}$I-ChTX displacement 20 mM salt | |
|---|---|---|---|---|---|---|
| drug | % maximum | IC$_{50}$ nM | % maximum | IC$_{50}$ nM | % of total | IC$_{50}$ nM |
| IMIDAZOLES: | | | | | | |
| Clotrimazole | 93 | 81.6 ± 70 | 87 | 143 ± 60 | 74.5 | 38.5 |
| Miconazole | 49 | 100 | 63 | 110 | 57 | 165 |
| Econazole | 31 | 575 | 47 | 270 | 37 | 205 |
| TRIAZOLES: | | | | | | |
| Fluconazole | 0 | — | 0 | — | 19 | — |
| NITROIMIDAZOLES: | | | | | | |
| Metronidazole | 28 | 850 | 36 | 440 | 49 | 580 |
| Ornidazole | 11 | — | 21 | — | — | — |
| Tinidazole | 21 | — | 3 | — | — | — |
| CHARYBDOTOXIN: | 95.5 | 0.096 | 52 | 0.360 | 74.5 | 0.033 |

*Results for clotrimazole are expressed as mean ± SD (n = 3 for $^{86}$Rb influx), and as the average of two experiments for displacement of $^{125}$I-ChTX. Data for charybdotoxin are the average of three experiments. Data for other drugs are from single experiments. IC$_{50}$ values were calculated with Dixon plot analysis.

To determine if the inhibition of Ca$^{2+}$-activated $^{86}$Rb flux was secondary to an inhibitory effect on the membrane Cl-permeability, the effect of the various compounds on the $^{35}$SO$_4$ influx was assessed. This assay is a measure of function of the major transport system for red cells, the AE1 (band 3) chloride/bichloride exchanger. No inhibition of AE1 function was found by any of these above mentioned compounds at 10 μM concentrations (Data not shown), suggesting that the inhibition of K+ transport cannot be explained by a concomitant inhibition of anion transport.

When the Gardos channel is activated, the increased permeability for K+ shifts the membrane potential away from the equilibrium potential for Cl- (E$_{Cl}$) toward the equilibrium potential for K+(E$_K$). This effect is magnified with the Cl-permeability is inhibited by DIDS. The effect of CLT on the membrane potential of SS cells in which the Gardos channel is activated is shown in FIG. 2. CLT markedly reduced K+ permeability and shifted E$_m$ from E$_K$ (theoretical values of −120 mVolt, assuming Internal K+ of 140 mM and external K+ of 1.5 mM) toward E$_{Cl}$ (theoretical and measured value of −9.0 and −7.5 mVolt, respectively). Moreover, the inhibitory potency of CLT was higher in low ionic strength conditions than in normal saline as appears in FIG. 1B.

2. Displacement of $^{125}$I-ChTX Binding to SS Erythrocytes By Imidazole Antimycotics $^{125}$I-ChTX is a specific ligand of the Ca$^{2+}$ activated K+ channel of human red cells. In normal red cells, 60-70% of the total binding can be displaced by an excess (50 nM) of cold ChTX (JGP absract). Specific binding of $^{125}$I-ChTX is heterogeneous in SS patients, with marked increase of maximum binding in the top, least dense fraction. To examine the interaction between CLT and the Ca$^{2+}$activated K+ channel of SS cells, the question whether CLT can displace $^{125}$I-ChTX (50 pM) bound to SS cells was tested. As shown in FIG. 3, CLT displaced $^{125}$I-ChTX in a dose-dependent manner. The ID$_{50}$(38.5 nM, average of two experiments) was in the same range as the ID$_{50}$ for inhibition of Ca$^{2+}$activated $^{86}$Rb influx (81.6±70 nM). Other 3. Ca$^{2+}$-Dependent Dehydration of SS Cells Induced by a 23187: Effect of Imidazole Antimycotics and Charybdotoxin Several protocols of deoxygenation have been used to demonstrate the role of the Ca$^{2+}$-activated K channel in promoting sickle cell dehydration [Glader, B. E. and D. G. Nathan, Blood 51:983-989 (1978); Bookchin et al., In *Approaches to the Therapy of Sickle Cell Anemia,* Les Editions INSEAM, Paris, 1986; p. 291-300; Ohnishi et al., Biochim Biophys. Acta 1010:199-203 (1989): Horruchi et al., Blood 71:46-51 (1988)]. However, the results are highly dependent on the protocol used for deoxygenation and reoxygenation of SS cells. We reasoned that the inhibitory effect of CLT and other antimycotics on the dehydration mediated by the Ca$^{2+}$-activated K+ channel should be assessed under conditions of maximal activation of this pathway. If the inhibitor is effective in blocking dehydration in these conditions, it should be able to block dehydration due to transient activation of the channel as during sickling. Accordingly, cells were exposed to A23187 in the presence of 100 μM CaCl$_2$ in a medium containing 140 mM NaCl, 4 mM KCl, at pH 7.40, with or without the transport inhibitors.

The inhibition by CLT was more pronounced than that by 50 nM ChTX, which also partially inhibited dehydration. After removal of ionophore and chelation of Ca, cell volume and hemoglobin concentration were measured on a cell per cell basis with the Technicon H-2 blood analyzer. FIG. 4 shows a typical plot of hemoglobin concentration (HC, x axis) versus cell volume (V, y axis) in the dual parameter histogram display in the upper panel, which is derived from the light scatter cytogram presented in the middle panel. Distribution histograms for red cell volume and hemoglobin concentration are presented in the lower panel. Arbitrarily established gates (hemoglobin concentration <28 and >41 g/dL; cell volume <60 and >120 fL) are used to define hypo- and hyperchromic cells and micro- and macrocytic cells, respectively. The distribution in the control SS cells (incubated with A23187 in the presence of 1 mM EGTA) resembles a teardrop, with reticulocytes and cells with low HC and high MCV in the top side of middle and left quadrant, discocytes in the central quadrant, and dehydrated dense cells in the right side of the middle quadrant. SS cells exposed to A 23187 and $Ca^{2+}$ were markedly dehydrated, as shown by the shift of the hemoglobin concentration (HC) histogram to higher values and by the increased HC values (FIG. 4). The presence of 10 μM CLT substantially prevented dehydration such that the HC and volume distributions of SS cells reverted nearly to those of control conditions. Measurements of cell cation content at the end of the incubation support the view that these effects are due to inhibition of K loss. Average values for three separate experiments in SS cells indicated that cell K was 279±20 mmol/Kg Hb in control; which decreased to 84.9±24 mmol/Kg Hb in the presence of $Ca^{2+}$; and was 210±30 mmol/Kg Hb and 192.8±39 mmol/Kg Hb in the presence of 10 μM CLT and 50 nM ChTX, respectively. Similar experiments were carried out with the other imidazole antimycotics, but the inhibitory effect on dehydration was substantially smaller than that observed by CLT and ChTX (data not shown).

C. Conclusions

1. The results and data demonstrate that imidazole derivatives are potent and specific inhibitors of the $Ca^{2+}$-activated K+ channel of sickle erythrocytes. Among the various members of this class of compounds, clotrimazole (CLT) appears to be the most potent inhibitor of the Gardos channel of sickle cells. CLT $IC_{50}$ values were obtained for inhibition of $Ca^{2+}$-activated K+ transport of 81.6±70 nM in low ionic strength medium and 143±60 nM in normal saline. Similar values were obtained for the inhibition by CLT of the membrane potential changes induced by activation of the Gardos channel in sickle erythrocytes. CLT also displaced 1251-ChTX, a specific ligand and for the $Ca^{2+}$-activated K channel of human red cells with an $IC_{50}$ (38.5 nM) similar to that of the inhibition of $^{86}Rb$ transport. CLT markedly inhibited the dehydration of sickle cells induced by pharmacologic activation of the Gardos channel using 60 μmol A23187/L cells and 100 μM $CaCl_2$ (see FIG. 3). The inhibition of CLT of K+ movement is believed not to be due to blockage of the anion permeability, since the influx of the anion $SO_4$ was not affected by CLT.

2. Other antimycotics as well as metronidazole, a chemically unrelated compound, were tested for their inhibitory potency on the Gardos pathway. Important differences were found in $IC_{50}$ for $^{86}Rb$ influx inhibition and in the maximal inhibition achieved with each of these compounds. The following sequence of inhibitory potency was obtained:clotrimazole>miconazole>econazole>metronidazole. Fluconazole was non-active as inhibitor of K+ transport. Moreover, the $IC_{50}$ values obtained in SS cells for miconazole (110 nM and econazole (270 nM) differ from considerably those obtained with a different method in normal AA cells (1.5 and 1.8 μM, respectively).

The present invention is not to be limited in form nor restricted in scope except by the claims appended hereto.

What we claim is:

1. A method for reducing sickle erythrocyte dehydration and delaying the occurrence of erythrocyte sickling, said method comprising the steps of:
    administering an effective amount of at least one compound selected from the class consisting of N-imidazole and N-nitroimidazole derivatives with no other heterocyclic moiety to the sickle erythrocytes in-situ; and
    allowing said administered compound to induce inhibition of the Ca-activated potassium channel at the membranes of said sickle erythrocytes in-situ such that sickle erythrocyte dehydration is reduced and the occurrence of erythrocyte sickling is delayed.

2. The method as recited in claim 1 wherein said imidazole derivative is one selected from the group consisting of clotrimazole, miconazole, econazole, butoconazole, oxiconazole and sulconazole.

3. The method as recited in claim 1 wherein said nitroimidazole derivative is one selected from the group consisting of metronidazole, tinidazole, ornidazole, and benznidazole.

4. The method as recited in claim 1 wherein said administration is per oral for a living human.

5. The method as recited in claim 1 wherein said administration is parenteral for a living human.

6. The method as recited in claim 1 wherein said administration is intravenous for a living human.

7. The method as recited in claim 1 wherein said administration is subcutaneous for a living human.

8. The method as recited in claim 1 wherein said administration is transmucosal for a living human.

* * * * *